(12) United States Patent
Pelkus

(10) Patent No.: US 8,353,882 B1
(45) Date of Patent: Jan. 15, 2013

(54) WOUND TREATMENT SYSTEM AND METHOD OF USE

(75) Inventor: Adrian Pelkus, San Marcos, CA (US)

(73) Assignee: Iyia Technologies, Inc., San Marcos, CA (US)

( * ) Notice: Subject to any disclaimer, the term of this patent is extended or adjusted under 35 U.S.C. 154(b) by 302 days.

(21) Appl. No.: 12/702,221

(22) Filed: Feb. 8, 2010

Related U.S. Application Data

(63) Continuation of application No. 11/087,383, filed on Mar. 22, 2005, now abandoned.

(60) Provisional application No. 60/555,568, filed on Mar. 22, 2004.

(51) Int. Cl.
*A61M 35/00* (2006.01)
(52) U.S. Cl. ........................ 604/290; 604/293
(58) Field of Classification Search .................. 604/290, 604/293
See application file for complete search history.

(56) References Cited

U.S. PATENT DOCUMENTS

| | | | |
|---|---|---|---|
| 3,101,716 A | 8/1963 | Cornell, Jr. | |
| 3,744,491 A * | 7/1973 | Fischer | ............................ 604/23 |
| 4,670,010 A | 6/1987 | Dragone | |
| 4,772,259 A | 9/1988 | Frech et al. | |
| 5,098,415 A | 3/1992 | Levin | |
| 5,312,385 A * | 5/1994 | Greco | ........................... 604/356 |
| 5,447,504 A * | 9/1995 | Baker et al. | .................... 604/289 |
| 5,848,998 A * | 12/1998 | Marasco, Jr. | ................... 604/290 |
| 6,273,906 B1 | 8/2001 | Swanson | |
| 6,443,978 B1 | 9/2002 | Zharov | |
| 7,771,402 B2 * | 8/2010 | Marasco | ........................ 604/293 |
| 8,048,044 B2 | 11/2011 | Stryker et al. | |
| 2006/0069357 A1 | 3/2006 | Marasco | |

OTHER PUBLICATIONS

International Search Report dated May 8, 2008, issued in International Appl. No. PCT/US06/28799.

* cited by examiner

*Primary Examiner* — Lynne Anderson
(74) *Attorney, Agent, or Firm* — Knobbe, Martens, Olson & Bear LLP

(57) ABSTRACT

A wound treatment system including a treatment chamber, a source of an aqueous antibiotic, a source of an oxygen-enriched gas, and a control system adapted to alternately surround a human limb with antibiotic mist and the oxygen enriched gas, which can be used to heal lesions such as foot ulcers. A method of treating lesions such as foot ulcers is also disclosed, that includes bathing the lesion in antibiotic mist and contacting it with oxygen gas.

20 Claims, 11 Drawing Sheets

WOUND TREATMENT SYSTEM AND METHOD OF USE

RELATED APPLICATION

This claims priority from U.S. Provisional Patent Application Ser. No. 60/555,568, filed Mar. 22, 2004, the entirety of which is incorporated herein by reference.

TECHNICAL FIELD

The present disclosure relates in general to wound treatment systems. More particularly, the present disclosure relates to a wound treatment apparatus and system for treatment of surface wounds.

BACKGROUND

Medical professionals and healthcare providers such as nurses and doctors routinely treat patients having surface wounds of varying size, shape and severity caused by skin ulcerations due to diabetes, venous stasis, post surgical infections, gangrenous lesions, decubitus ulcers, amputations, skin grafts, burns, and frostbite. Variations in wound type and other patient indications dictate variations in desired medications for treatment, such as antibiotics, growth factors, enzymes, hormones, protocols, such as delivery rates for medication and temperature control.

One particular area of concern involves foot or limb wounds in diabetic patients. It is known that foot wounds in diabetic patients represent a significant public health problem throughout the world. Diabetes is a large and growing problem in the United States and worldwide, costing an estimated $45 billion dollars to the U.S. health care system. Patients afflicted with diabetes often have elevated glucose and lipid levels due to inconsistent use of insulin, which can result in a damaged circulatory system and high cholesterol levels. Often, these conditions are accompanied by deteriorating sensation in the nerves of the foot. As a result, diabetics experience a high number of non-healing foot ulcers.

It is estimated that each year up to three million leg ulcers occur in patients in the U.S., including venous stasis ulcers, diabetic ulcers, ischemic leg ulcers, and pressure ulcers. The national cost of chronic wounds is estimated at $6 billion. Diabetic ulcers often progress to infections, osteomyelitis and gangrene, subsequently resulting in toe amputations, leg amputations, and death. In 1995, approximately 70,000 such amputations were performed at a cost of $23,000 per toe and $40,000 per limb. Many of these patients progress to multiple toe amputations and contralateral limb amputations. In addition, the patients are also at a greatly increased risk of heart disease and kidney failure from arteriosclerosis which attacks the entire circulatory system.

The conventional methods of treatment for non-healing diabetic ulcers include wound dressings of various types, antibiotics, wound healing growth factors, skin grafting including tissue engineered grafts, use of wheelchairs and crutches to remove mechanical pressure, and finally amputation. In the case of ischemic ulcers, surgical revascularization procedures via autografts and allografts and surgical laser revascularization have been applied with short term success, but with disappointing long term success due to reclogging of the grafts. In the treatment of patients with venous stasis ulcers and severe venous disease, antibiotics and thrombolytic anticoagulant and anti-aggregation drugs are often indicated. The failure to heal and the frequent recurrence of these ulcers points to the lack of success of these conventional methods. Accordingly, the medical community has a critical need for a low cost, portable, non-invasive method of treating diabetic, venous, ischemic and pressure ulcers to reduce mortality and morbidity and reduce the excessive costs to the health care system.

Most problematic of all is that treatment of diabetic foot ulcers has been focused on amputation and not on limb salvage, as many of the wounds have not been properly treated. Improper treatment can be attributed to lack of an easy and inexpensive treatment system and method and severe inconvenience to the patient in using current methods. There is a need to prevent amputation by healing such wounds, particularly at an early stage.

Furthermore, amputation for conditions such as foot ulcers and frostbite becomes less avoidable the longer the condition is either left untreated or is unsuccessfully treated. Therefore, it is crucial to apply an effective treatment regimen as soon as possible. Unfortunately, foot wounds in patients with, for example, diabetes develop because of a process called neuropathy. Diabetes causes loss of sensation such that skin injury and complete breakdown (ulcer) can develop with no or minimal pain. These wounds tend not to heal because of ongoing mechanical trauma not felt at all by the patient as painful. Therefore, by the time the patient discovers the wound, the wound has often progressed so that the patient's treatment options have become severely limited.

In many cases, such wounds can only be healed by protecting them from mechanical trauma. Small plantar ulcers in diabetic patients area usually seen by primary care practitioners and endocrinologists. The present method for healing plantar ulcers is a total contact cast for the foot, which provides complete mechanical protection. This method is not ideally suited for either of these practice settings, because it requires skilled and specialized care in application, along with frequent follow up. Most patients perceive the cast to be an inconvenience at the early stages of such a wound, while perceiving that such a wound is not a serious matter. The alternative to the cast is to ask the patient to be non-weight bearing through the use of a wheelchair, crutches, or a walker, which provide complete mechanical protection only with complete patient compliance. This alternative rarely proves to be effective in healing wounds within a reasonable time period.

What is needed is a treatment that primary care physicians and their staff can employ to treat ulcers and other wounds that does not require extended physician time and that is effective even at later stages of wound progression. Also, what is needed is a treatment that allows patients to be able to continue their active lives without the need to wear casts, or be confined to wheelchairs and crutches.

SUMMARY

In one embodiment, a wound treatment apparatus includes a treatment vessel having a treatment chamber and an opening to the treatment chamber that are sized to receive a human limb. A removable and substantially gas impermeable liner lines the chamber of the vessel and forms a treatment zone around the patient's limb. A cuff is removably coupled to the opening of the vessel and is sized to sealingly engage a human limb when the limb is inserted through the opening. A mixture tank holds a humidifying agent and is in fluid communication with the chamber of the vessel. A first array of light emitting diodes is coupled to the chamber and emits ultraviolet light into the chamber. A speaker is attached to the vessel and delivers low frequency sound waves to the chamber. A second array of light emitting diodes is coupled to the chamber and emits pulsed light into the chamber.

A wound treatment system includes a vessel that is sized to receive a human limb. The vessel includes a chamber with an opening leading into the chamber. A removable liner lines the chamber of the vessel and forms a treatment zone. A humidifier in fluid communication with the treatment zone humidifies a solution of water and antibacterial agent. An oxygen source is in fluid communication with the treatment zone. A speaker is coupled to the vessel and emits low frequency sound waves to the chamber. A first array of light emitting diodes that emits ultraviolet light is coupled to the vessel near the opening of the treatment chamber. A second array of light emitting diodes that emits pulsed light into the chamber is coupled to the chamber. The system also includes a control panel.

A wound treatment method for treating a wounded limb is also described. The method includes cleaning the wound. The method also includes disinfecting the limb by passing the limb through a ring of ultraviolet light emitting diodes that emit ultraviolet light on the limb as the limb passes through the ring. The limb is placed into a vessel having a chamber that is lined with a substantially gas impermeable liner by passing the limb through a cuff that sealingly surrounds a portion of the limb, thus forming a substantially gas impermeable treatment zone around a portion of the limb distal the cuff. The limb is heated by introducing warm water into the chamber, which causes the inner liner to collapse around the patient's limb. The warm water is emptied out of the chamber, and a temperature controlled mist of topical hyperbaric oxygen, water and an antibacterial solution is introduced into the treatment zone. The limb is massaged by activating a speaker coupled to the vessel that transmits low frequency sound waves to the treatment zone. The limb is heated and kept warm by activating an array of light emitting diodes coupled to the vessel that emits pulsed light onto the limb.

DESCRIPTION OF DRAWINGS

These and other features and advantages will be apparent from the following more particular description thereof, presented in conjunction with the following drawings, wherein.

DETAILED DESCRIPTION

The apparatus, systems, and methods described herein provide hyperbaric oxygen to open, chronic wounds as an adjunct therapy in wound management and treatment. In addition, per determination by the healthcare providers that use the described apparatus, systems, and methods, they can also provide mild heat, gentle massage, infrared and ultraviolet light therapy, moisture therapy, and application of antibacterial agents. These features are intended to promote the rate of healing and suppression of bacterial growth.

Figure 1:
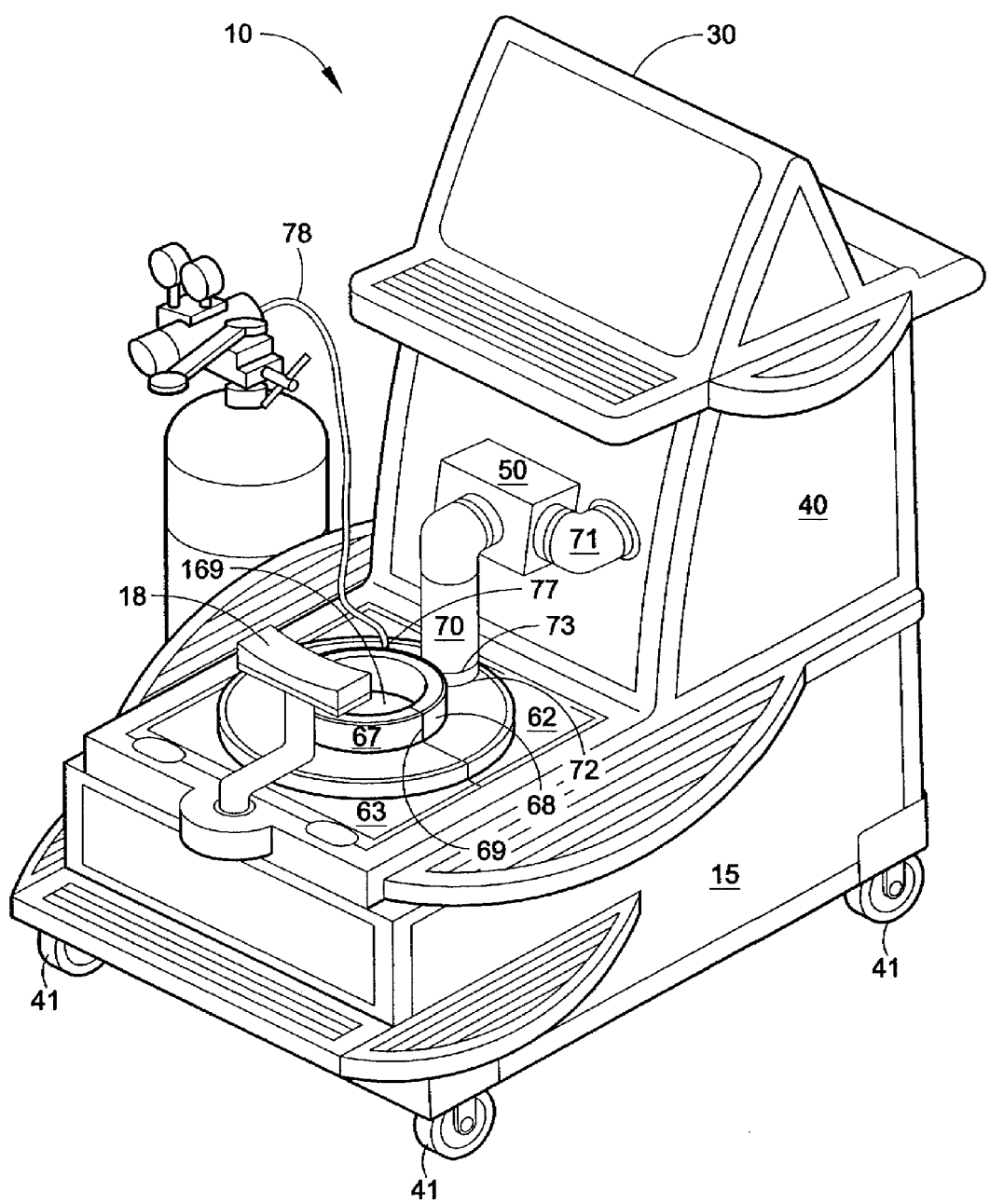
FIG. 1 is a three-dimensional view of a wound treatment system.

Turning to FIG. 1, a wound treatment system 10 is shown, which generally includes a topical oxygen chamber for limbs and is intended to surround a patient's limb and apply humidified water, antibacterial agent, and oxygen topically at a pressure slightly greater than atmospheric pressure. The wound treatment system 10 includes a rectangular, rigid plastic carriage 15 having a treatment vessel 800 forming a chamber 810 (shown in FIG. 5) that is sized to accommodate a patient's limb, particularly a patient's foot and a portion of the leg up to the knee. A padded leg rest 18 supports the patient's leg during treatment sessions. The system also includes a control panel 30, a cart 40 housing a first reservoir 600 for water, an adiabatic humidifier 400 that holds a solution of water and antibacterial agent, a water pump 500 (all shown in FIGS. 8A and 8B), and a control box (beneath the control panel) that houses the circuit boards that control the system 10. A mist control valve unit 50 is attached to a back panel of the cart 40. A hose 70 connects the mist control valve unit 50 to the vessel 20, and one or more hoses 71 connect the humidifier 400 to the mist control valve unit 50.

Covering the vessel 800 is a lid assembly 60 (shown in FIGS. 1 and 4A) that includes a first lower lid 61 that is hinged to the vessel 800 at the proximal end 64 of the vessel 800 opposite the end abutting the back panel of the cart 40. The lower lid 61 includes a circular opening 161 that provides access to a chamber 810 formed inside the vessel.

Figure 4A:
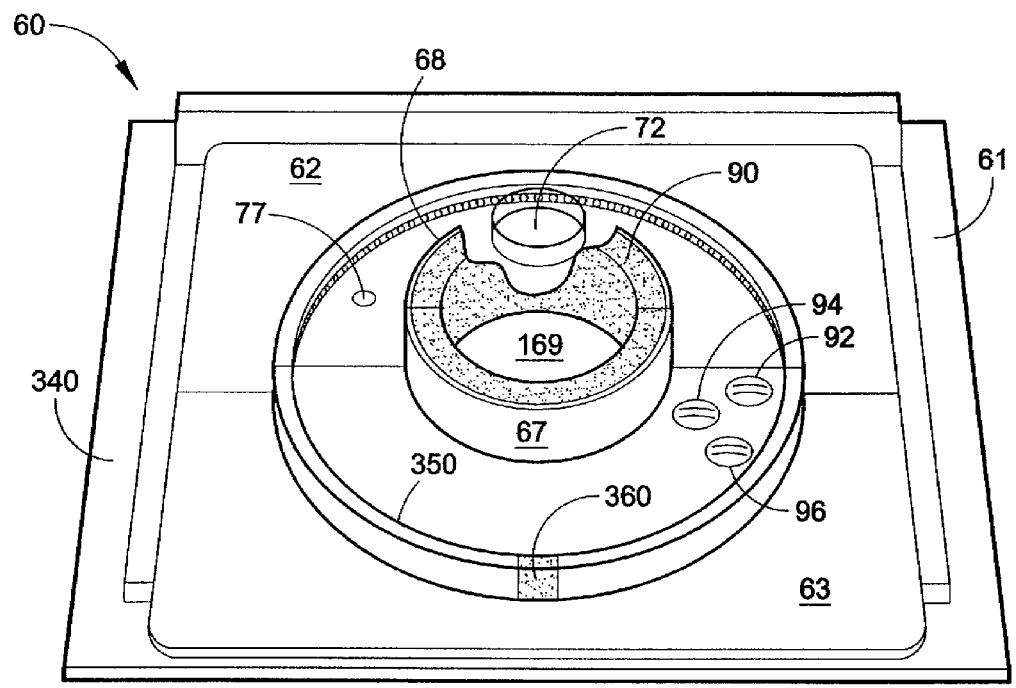
FIG. 4A is a three dimensional view of a lid assembly of a wound treatment system.

The lid assembly 60, as shown in FIGS. 1 and 4A, also includes a second upper lid that is formed by two opposing covers 62 and 63. Cover 62 covers the distal side 64 of the vessel 800 and cover 63 covers the proximal side 65 of the vessel 800. The covers 62 and 63 are completely removable from the top of the vessel 800. The distal side of cover 63 forms a half circular indentation that is matched by a half circular indentation in the proximal side of cover 62 so that when the distal side of cover 63 and the proximal side of cover 62 join, a round opening 169 is formed when the covers 62 and 63 are secured over lid 61. Each cover 62 and 63 has a raised half circular wall 67 and 68 projecting vertically from its top surface around its corresponding half circular indentation. When the covers are joined as shown in FIG. 1, the walls 67 and 68 join to form a cylinder 69. The round opening 169 formed when the half circular indentations are joined is concentric with the circular opening 161 of the lower lid 61 so that a patient's limb can project down through the cylinder 69, through opening 169 formed by the covers 62 and 63, through opening 161 of the lower lid 61, and into the chamber 830 of the vessel 20.

Figure 4B:
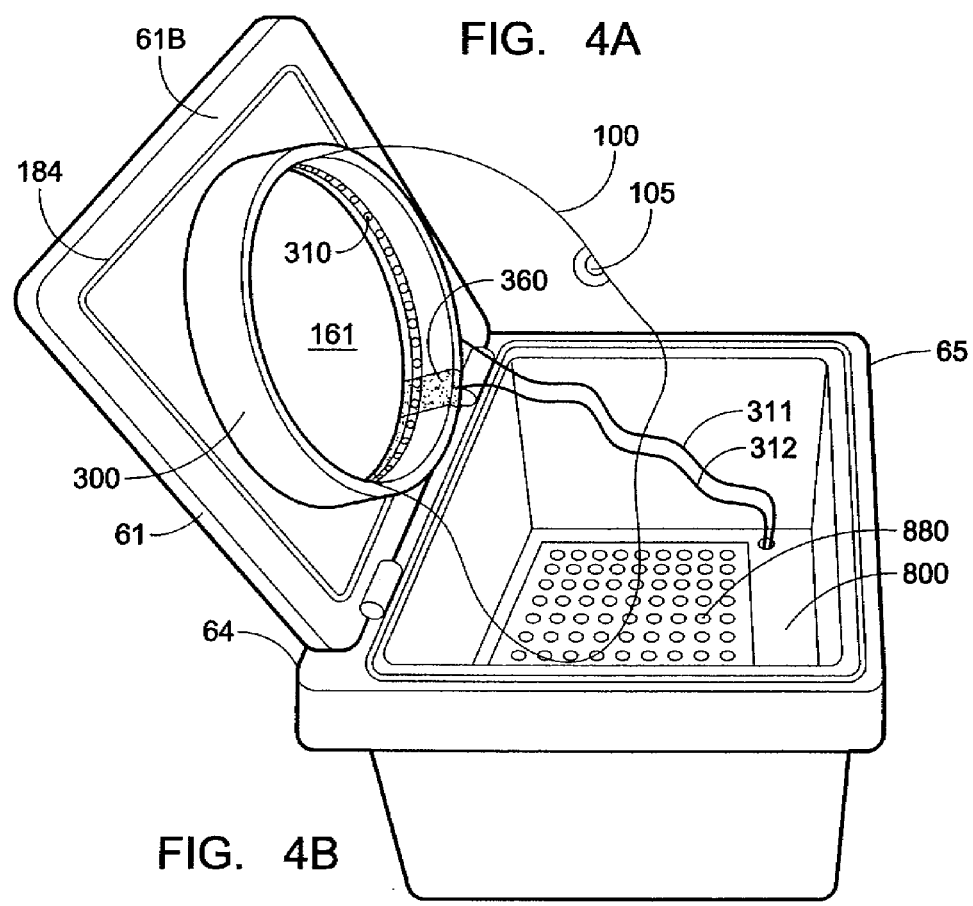
FIG. 4B is a three dimensional view of a treatment vessel of a wound treatment system.

An oxygen inlet port 77 on the cover 62 (or alternatively cover 63) receives a hose 78 connected to an oxygen source, such as an oxygen tank or a central oxygen source in a hospital. The inlet port 77 can include a fitting (not shown) to sealingly secure the hose 78 to the cover 62. The cover 62 includes a vapor inlet port 72 that receives the hose 70. The vapor inlet port 72 can include a fitting 73 to sealingly secure the hose 70 to the vapor inlet port 72. Either of the covers 62 or 63 can also include a temperature sensor 92, a humidity sensor 94, and a pressure sensor 96, each of which are in fluid communication with a treatment zone formed by a treatment bag 100 sealed to the lid 61 of the vessel (FIG. 4B). The cart 40 includes wheels 41 at each corner to mobilize the system 10.

Figure 2:
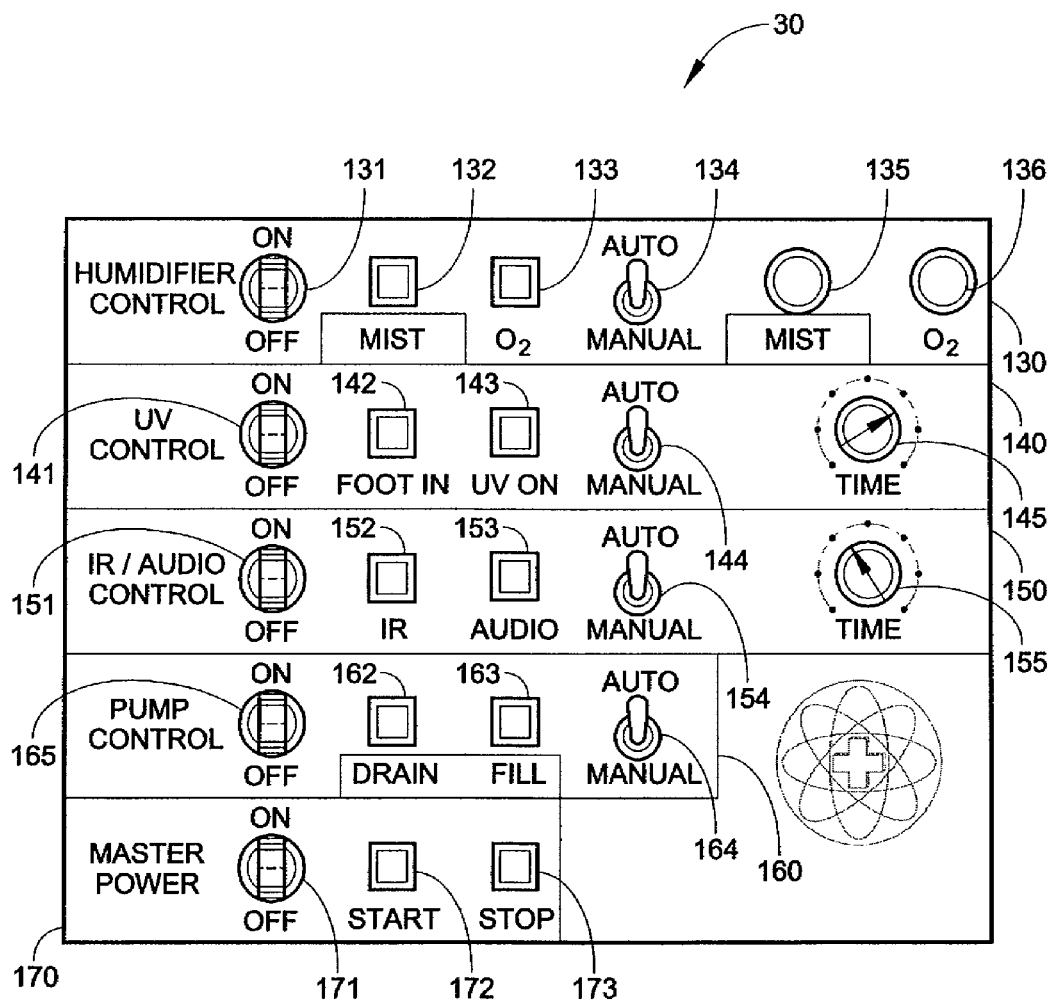
FIG. 2 is a is an illustration of a control panel of a wound treatment system.

As shown in FIG. 2, the control panel 30 includes a display with various knobs and switches that controls the operation of the wound treatment system 10. The panel includes controls 130 that control the humidifier, controls 140 that control an array of ultraviolet light emitting diodes (LEDs) 310 (see FIGS. 4A and 4B) controls 150 that control an array or board of infrared light 880 (see FIGS. 4B, 6A, and 7A) and an audio transducer or speaker 870 (see FIG. 5, 6A, 7A, and 7B), controls 160 that control a water pump 500 (see FIG. 8A), and controls 170 that control the master power for the system 10.

The humidifier functions of the system are controlled by controls 130, which include at least some of the following: an on/off switch 131 that turns on the humidifier function; a button 132 that can be used to manually activate or open the mist control valve unit 50 and that illuminates when the mist control valve unit 50 is open and allowing the flow of therapeutic mist into the chamber 830; a button 133 that opens an electronic oxygen flow valve in the tubing 78 connected to the oxygen source and illuminates when the oxygen flow valve is open and allowing oxygen flow into the chamber 810; an auto/manual switch 134 that sets the humidifier function to either manual operation or auto operation; a mist timer knob 135 that is used to set the amount of time for mist flow into the chamber 810; and an oxygen timer knob 136 that sets the amount of time for oxygen flow into the chamber 810.

The UV functions of the system is controlled by controls 140, which include at least some of the following: an on/off switch 141 that turns on the UV function; a foot in button 142 that illuminates when the patient inserts his foot through the opening 169—the collar 300 can have a sensor 360 that senses the foot and sends a signal back to the control box to activate the UV LEDS; a UV on button 143 that can be depressed to manually activate the UV LEDS 310 and that illuminates when the UV LEDS 310 are activated; an auto/manual switch 144 that sets the UV function to either manual operation or auto operation; and an UV timer knob 145 that sets the amount of time that the UV LEDS will remain on once they are activated.

The IR/Audio functions of the system is controlled by controls 150, which include at least some of the following: an on/off switch 151 that turns on the IR/Audio function; an IR button 152 that can be used to manually activate the IR LEDS and that illuminates when the IR LEDS and speaker are operating; an Audio button 153 that can be used to manually activate the speaker or audio transducer and that illuminates when the speaker is operating; an auto/manual switch 154 that sets the IR/Audio function to either manual operation or auto operation; and a timer knob 155 that sets the amount of time that the IR LEDS and speaker will remain on once they are activated.

The pump control functions of the system is controlled by controls 160, which include at least some of the following: an an/off switch 161 that turns on the pump control function; a drain button 162 that can be used to manually operate the timing of drainage of the chamber 810 and that illuminates when the chamber 810 is draining; a fill button 163 that can be used to manually operate the timing of filling the chamber 810 with warm water and that illuminates when the chamber is filling with water; and an auto/manual switch 164 that sets the pump control function to either manual operation or auto operation.

The master control buttons 170 include at least some of the following: a master control switch 171 that turns the system on and off; a start button 171 that is used to start the operation of the system and that illuminates when the system is operating; and a stop button 172 that can be depressed to prematurely stop the operation of the system.

In one embodiment, the control panel 30 also includes a thermostat (not shown) that is electrically coupled to a submergible water heater 680 (see FIG. 9A) that is located in the water reservoir tank 600. The thermostat can be used to control the temperature of the water that is pumped from the water reservoir tank 600 into the chamber 810.

In operation, the system 10 works by switching the master power switch 170 to the on position, which turns the system on and puts the system in ready mode. The healthcare provider then decides which of the functions will be used in the specific regimen for the particular patient. Depending on the patient and the ailment, the regimen may provide for operation of all of the functions, or just some of the functions. For example, a regimen may call for warming the limb with injection of warm water into the chamber and then treating the wound with the antibiotic mist, but may not require infrared treatment and low frequency sound vibrations. Thus, all of the on/off switches would be switched to the one position except for the IR/Audio control switch 151, which would remain in the off position. When operating under normal conditions, all of the functions can be turned on by switching all of the on/off switches to the on position. This sets all of the functions to ready mode. The mist timer knob 135 and oxygen timer knob 136 can then be set to operate for the appropriate amount of time. According to one embodiment, the mist can be set at about fifteen minutes, while the oxygen is set at about five minutes. The UV timer knob 145 is set to operate for an appropriate amount of time. According to one embodiment, the UV timer is set to operate for less than 5 seconds, less than 4 seconds, less than 3 seconds, less than 2 seconds, or less than 1 second. The IR/Audio timer can be set to operate fora period of time coinciding with the warm water bath of the limb, which is when the chamber is filled with warm water, which warms the limb. This period can last from about one minute to about ten minutes or more. All of the auto/manual switches can be set to auto for a predetermined and default regimen. Next the healthcare provider depresses the start button 171, which begins the regimen.

According to one embodiment, when all of the functions are in operation and auto modes, and the start button 171 is depressed, the system operates as follows. First the system waits for the sensor 360 to detect the insertion of a limb of a patient P, as shown in FIG. 3B) into the chamber 810. After the wound in the limb is cleaned, the limb is inserted through the opening 169 of the covers 62 and 63 and the opening 161 of the lid 61. The sensor 360 detects the limb as it passes through the opening 161 and activates the UV function, which activates the ring of UV LEDs 310 located concentrically around the opening 161. The UV LEDS 310 briefly stimulate the limb (about one to five seconds) as it passes through the opening of the chamber 810 and then the UV LEDs 310 deactivate. The UV on button 143 illuminates while the UV LEDs are on.

Next, a cuff 90 is placed around the limb and the lids 62 and 63 closed around the cuff 90 so that the half circular walls 67 and 68 form a substantial seal around the cuff. The cuff will be discussed in more detail later. The limb is placed in a bag or liner 100 that is substantially impermeable to gas. The top opening of the bag 100 is sealed to the bottom surface of the lid 61 and forms an airtight seal with the bottom surface of the lid 61. Thus, when the limb is surrounded by the cuff 90, which is surrounded by the half circular walls 67 and 68, the portion of the limb distal the cuff is inside the bag in a substantially sealed treatment zone.

Once the limb is secured as described, the pump 500 is activated and pumps warm water from the water reservoir 600 to the chamber 810 of the vessel 800 through a hose 510 that is connected to an outlet port 660 in the reservoir 600 on one end and the pump 500 on the other end. Another hose 520 carries the water from the pump 500 to a water pipe protruding from the vessel 20 that is connected to an opening in the chamber 810. The water pump 500 shuts off automatically after a predetermined amount of water is drained from the reservoir 600. The warm water entering the chamber 810 causes the bag 100 to collapse around the limb and creates a warm southing sensation on the limb. The warm water bath remains in the chamber 810 for a predetermined amount of time, generally between about one minute and ten minutes or more. The array of IR LEDs 880 in the chamber 810 is activated and transmits a pulsed (or steady) IR light during the warm water bath. The IR LEDS further warm the limb increasing circulation.

Also contemporaneous with the activation with the IR LEDs 880, the audio transducer or speaker 870 is activated and generates a low frequency sound wave that surrounds the limb. This creates a massaging effect, stimulates the skin and further enhances circulation. The water pump 500 is then activated in reverse and the warm water is pumped out of the chamber 810 and back into the reservoir 600. The IR LEDs 880 and the audio transducer 870 are turned off.

An adiabatically-humidified, temperature-controlled vapor of water and a topical antibacterial, antiseptic or antibiotic agent is released from the humidifier 400 by mist control valve unit 50. The vapor travels through the tube 70 and enters the treatment zone through a port 72 in the lid 62, which is substantially sealed to the tube 70. The vapor hydrates the wound and provides antibacterial effects. This vapor treatment can last between about two minutes and about thirty minutes, depending on the timer 135 set by the healthcare provider. In one embodiment, vapor treatment lasts about fifteen minutes. Then the mist control valve unit 50 is activated to close the valve between the humidifier 400 and the tube 70.

At this time, the oxygen release valve is opened and oxygen flows from the oxygen source, which can either be an oxygen tank as shown or a wall mounted oxygen unit connected to a central oxygen source, such as in a hospital setting (not shown). The oxygen flows through the tube 78 into an oxygen inlet port 77 on the surface of the lid 62. The oxygen displaces the vapor and oxygenates the wound. Oxygenation can last between about one minute and about fifteen minutes. In one embodiment, oxygenation lasts about five minutes. The process between vapor treatment and oxygenation can be repeated several times. In one embodiment, vapor treatment and oxygenation are repeated three times for a total of four rounds of treatment lasting approximately eighty minutes. The patient's oxygen level can be monitored during treatment using an oximeter connected to the patient's finger or other body part. The oximeter can be electrically connected to the control circuits in the control box of the system 10, and a display can warn the user to stop treatment or introduction of oxygen if the patient's blood oxygen level is too low or too high according to a predetermined level, such as below 80% saturation for an extended period of time. An extended period of time can be two or more minutes.

Figure 3A:
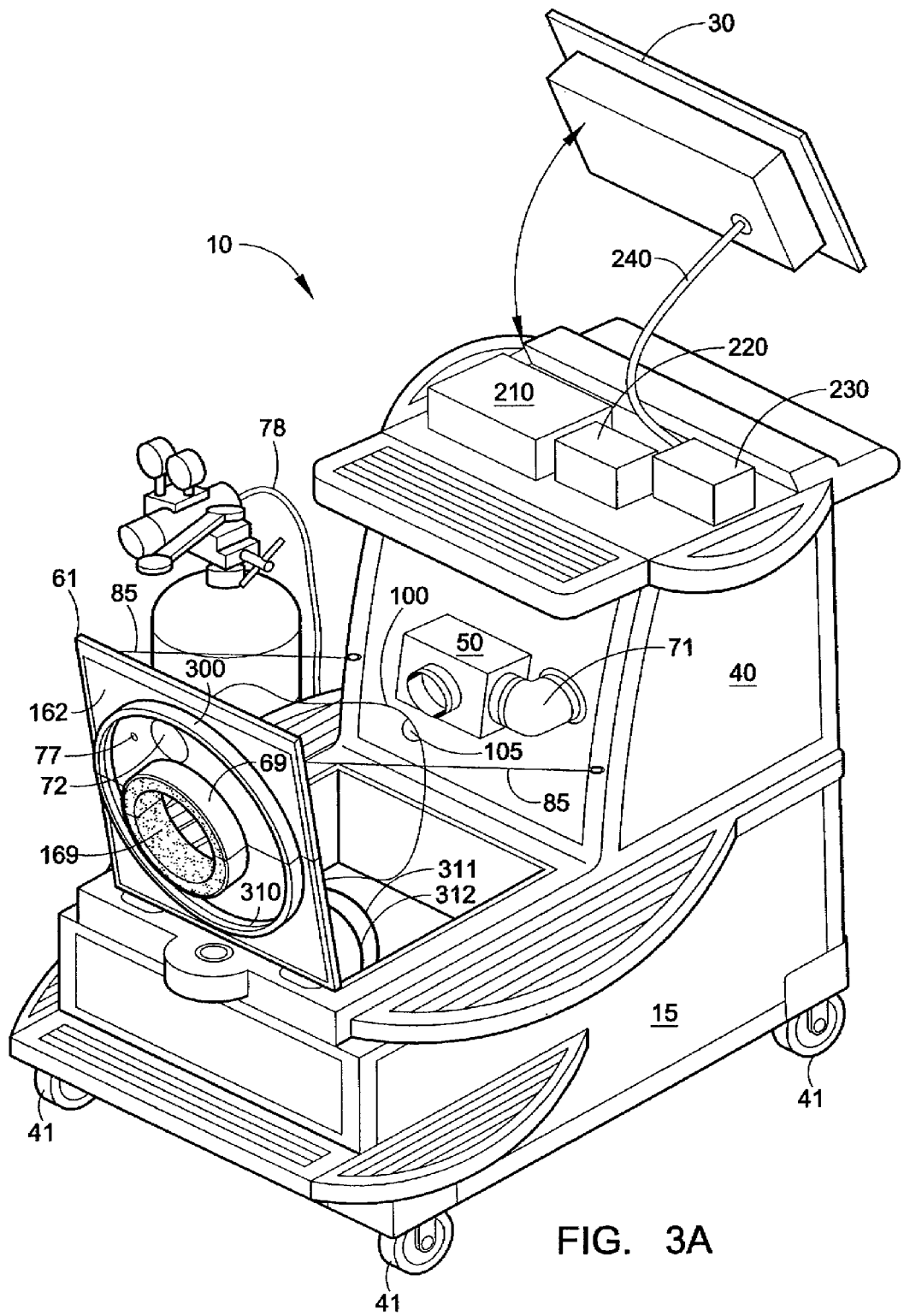
FIG. 3A is another three-dimensional view of the wound treatment system depicted in FIG. 1.
Figure 3B:
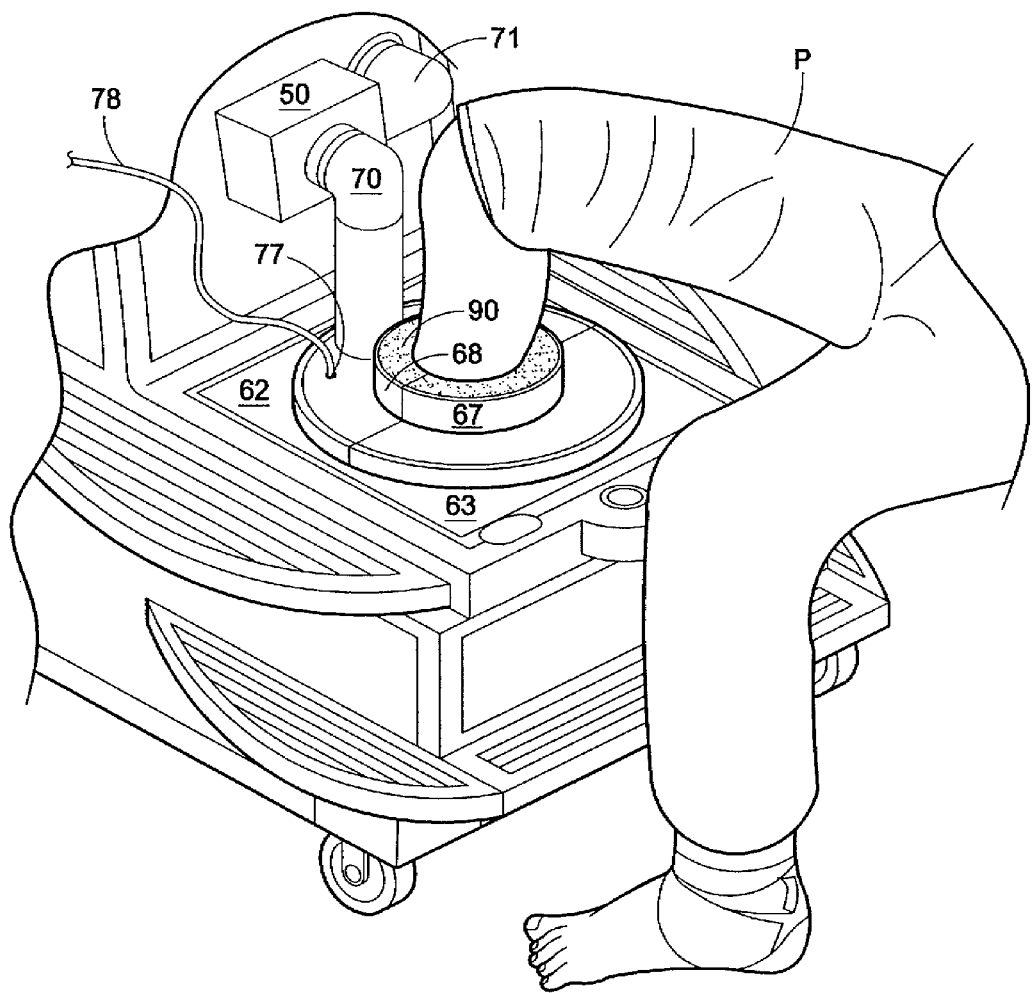
FIG. 3B is a three dimensional view of the wound treatment system depicted in FIG. 1 with patient being treated.

FIG. 3A shows the wound treatment system 10 with the control panel 30 lid removed and the lid 61 opened. Underneath the lid of the control panel reside the various electronics and circuitry of the system 10. A 12V power supply 220 can be used to power the system. A sweep function generator 210 is used to generate a low frequency waveform for the audio function. The sweep function generator 210 can generate an adjustable frequency of between about 1 Hz and about 1000 Hz. It can generate various types of waveforms, such as sweeping waveforms and ramping waveforms within that range of frequencies. The sweep function generator 210 produces a sin wave signal that is transmitted to the audio amplifier 230, which can be a 12V amplifier. The amplifier 230 amplifies the signal to about 50 W and transmits the amplified signal to the speaker or audio transducer 870 connected to the vessel 800. The sweep function generator 220 can be preset to a default frequency and waveform. In one embodiment, it can be preset to generate a 60 Hz signal, which can be manually altered to produce a signal at other frequencies between the range of about 1 Hz and about 1000 Hz. An assembly control cable 240 connects the control box (not shown) with the electronic components of the system. The control box (not shown), which is housed underneath the control panel lid 30, houses all of the circuit boards required to operate the system 10.

In one embodiment, as shown in FIGS. 3A and 4B, on the bottom surface 61B of the lid 61 is a circular collar 300 that forms a perimeter around the opening 161 on the bottom surface 61B of the lid 61. An array of UV LEDs 310 is mounted on the inner surface of the collar forming a ring. The UV LEDs 310 each point toward the center of the opening 161. There can be as few as four LEDS and as many as one hundred twenty or more LEDs in the array of UV LEDs 310. The array of UV LEDs 310 can deliver 330 W of UVA at about 320 nm to about 400 nm. Alternatively, or in addition to, the array of UV LEDs 310 can deliver 330 W of UVB at about 290 nm to about 320 nm. Alternatively, or in addition to, the array of UV LEDs 310 can deliver 330 W of UVC at about 100 nm to about 200 nm. In one embodiment, there are ninety UV LEDs delivering 330 W of UVA at about 374 nm to about 392 nm, delivering a total of about 324 mW or 324 W. The collar 300 also includes a motion sensor 360 to detect when a limb has been inserted through the collar and the ring of UV LEDs 310. The motion sensor is connected to the control box through a wire 312 that is threaded through a hole in the collar and then a hole in the bottom of the carriage 15 and up through the bottom of the cart 40. The wire 312 is eventually bundled in the cable 240 and carries an electrical signal to the circuitry in the control box. The array of UV LEDs 310 receives its electrical signals from the control box through a wire 311 that is also threaded through the hole in the collar and then a hole in the bottom of the carriage 15 and up through the bottom of the cart 40 and eventually bundled in the cable 240.

The lid 61 is raised by lifting the distal side of the lid while the proximal side pivots along its hinges. Chains or wires 85 are connected at one of their ends to the bottom surface 61B of the lid 61 and at their other ends to the back panel of the cart with hooks or other securement means. The lid 61 falls back and is supported by the chains 85. The bottom surface 61B of the lid 61 includes a gasket 184 around it's square or rectangular perimeter that seals the bottom surface 61B of the lid 61 to the vessel 800 when the lid 61 is closed.

As shown in FIG. 4A, the lid 61 can have a substantially circular crown 350 projecting vertically from its upper surface 340. This crown is in lieu of the collar 300 shown in FIGS. 3A and 4B. The array of UV LEDs 31.0 is coupled to the inside surface of the crown 350, as is the motion detector 360. The upper lid is formed by covers 62 and 63. Each of the covers 62 and 63 can form a corresponding half washer shaped raised portion 62 and 63. Projecting vertically from the center of each raised portion 62 and 63 is a half circular wall 67 and 68. When the covers 62 and 63 are placed over the lid, the washer shaped raised portions 62 and 63 join to form a raised washer shaped portion that fits over the circular crown 350 to form a substantial seal between the outer wall of the crown 350 and the inner wall of the washer shaped raised portion. The outer wall of the crown 350 can include a gasket (not shown) to reinforce the seal. The half circular walls 67 and 68 also join to form a cylinder with an opening 169 in the center that is concentric with and open to the opening 161 of the lid 61.

An oxygen inlet port 77 on the washer shaped raised portion 62 (or alternatively on washer shaped raised portion 63) receives a hose (not shown) connected to an oxygen source, such as an oxygen tank or a central oxygen source in a hospital. The oxygen inlet port 77 can include a fitting (not shown) to sealingly secure the hose to the cover raised portion 62. The raised portion 62 includes a vapor inlet port 72 that receives the hose 70 (shown in FIG. 1). The vapor inlet port 72 can include a fitting 73 (shown in FIG. 1) to sealingly secure the hose 70 to the vapor inlet port 72.

There are only two components of the wound treatment system 10 that make physical contact with the patient's skin: a liner or bag 100 (as shown in FIGS. 3A and 4B) into which the patient's limb is placed; and a foam cuff 90 (as shown in FIGS. 3B and 4A), which is placed around the patient's limb.

The liner 100 forms a treatment zone around the wound and makes contact with the open wound. Therefore, it is preferable that the liner 100 be biocompatible and sterile. The liner 100 can be discarded or sterilized after each use and/or replaced with a new or sterilized liner 100.

The material from which the liner 100 is made can be any strong substantially gas impermeable material. Extruded flexible plastic film material, such as polyethylene (hdpe, Idpe, Ildpe, polyprolene, etc,), polyurethane ether or ester open cell foam (e.g., United States Plastics Corp. Stock No. 47154), polyethylene terephthalate, polyvinyl chloride, or ethylene/polyvinyl copolymer sheet stock, and vapor proof treated fabric, such as nylon, are suitable. The material can be puncture resistant and transparent. The flexible sheet material can have a variety of shapes. It can be a single layer, such as a bag to surround a limb, or have multiple layers. The bag or liner 100 may also be co or tri axially oriented.

The term "substantially gas impermeable", as used herein with respect to the sheet material, means gas impermeable to the extent needed to prevent excessive gas escape from the treatment zone through the sheet material. Total gas impermeability seldom is needed, particularly for continuous flow treatment devices. However, generally high impermeability is desirable for static treatment devices.

The perimeter of the opening of the liner 100 can have an adhesive strip with a removable backing. The backing can be removed and the perimeter of the lining can be substantially sealed against the crown 350 (or the collar 300), thus forming a sealed connection between the perimeter of the opening of the liner 100 and the lid 61. Alternatively, the liner 100 can be taped to the crown 350 (or the collar 300) to form a substantial seal between the lid 61 and the liner 100.

In one embodiment, the liner 100 includes a pressure release valve 105 built into it. The design of the pressure release valve 105 is not critical. Many different types are suitable. For example, the valve 105 can be a ball valve or a baffle valve such as a flap or butterfly baffle valve. Other valves are equally suitable, so long as they are capable of accurately setting the maximum release pressure and are inexpensive and so discardable. If desired the adjustable valve 105 can be calibrated to show the pressure setting. In one embodiment, the maximum release pressure can be set at 22 mm of mercury so that the pressure inside the liner 100 never surpasses that amount of pressure. The valve body can be made of any rigid plastic, although metals such as stainless steel can be used also. The spring can be steel or plastic. Very inexpensive completely plastic valves can be used as well.

The pressure release valves 105 integrated with the liner 100 are inexpensive yet reliably accurate, within the preferred accuracy ranges. If desired, they can be removed from a used liner 100 and reused on new liners. Using a valve that is in communication with the treatment zone and not with the gas supply eliminates the need for a separate pressure control mechanism between the chamber 810 and the oxygen source. The chamber 810 can be connected directly to a gas or oxygen tank or a hospital gas supply line.

With any of the embodiments described herein, a foam cuff 90, as shown in FIG. 3B, is placed around the patient's limb and inserted concentrically with the cylinder formed by the half circular walls 67 and 68. The foam cuff 90 can be disjoined so that it can be opened and placed around a limb. The foam cuff 90 can be made of a biocompatible open cell material that is compressible and resilient and forms a substantial seal or baffle between the patient's limb and the cylinder formed by the walls 67 and 68. The open cell configuration prevents rapid fluid leakage through the cuff, but does allow for some fluid leakage at pressures approaching 22 mm of mercury, thus acting as a baffle. The pressure inside the treatment zone should not reach 22 mm of mercury, and the fluid leakage through the foam cuff 90 as the pressure inside the treatment zone increases will prevent pressures from building up beyond that level. Thus, with the use of an open cell material in the foam cuff 90, a pressure release valve 105 in the liner 100 may not be necessary. The foam cuff 90 can also include a backing on its outer non-skin contacting surface that can be peeled away, exposing a sticky surface that sticks to the cylinder. The foam cuff 90 can be made of a polyurethane ester or a natural material.

Figure 5:
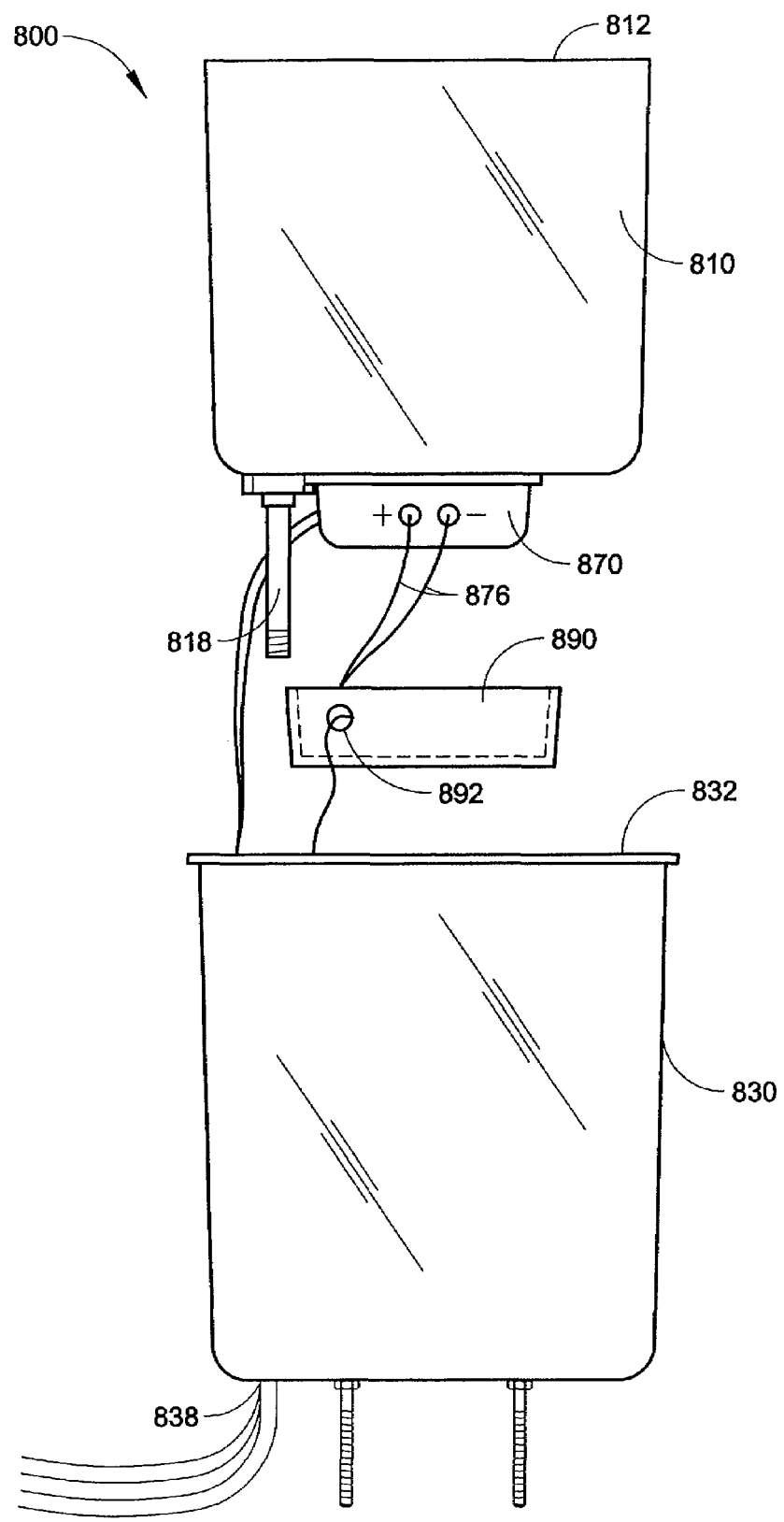
FIG. 5 is a side exploded view of a treatment vessel of a wound treatment system.

FIGS. 5-7B show the vessel 800 in which the patient's wound is treated. The vessel 800 sits inside of the rigid plastic carriage 15 shown in FIG. 1. As shown in FIGS. 5 and 6A, the vessel 800 is formed by inserting chamber 810 into tank 830. The outer dimensions of the chamber 810 are slightly smaller than the inner dimensions of the tank 830 so that the chamber 810 is nested securely within the tank 830. The only dimension of the tank 830 that is substantially different from the chamber 810 is that the tank 830 is several inches deeper than the chamber 810. This provides for extra room at the bottom of the tank 830 for the audio transducer or speaker 870 connected to the bottom of the chamber 810, so that when the chamber 810 is placed in the tank 830, the top edges 812 and 832 of the chamber 810 and tank 830 are substantially coplanar as shown in FIG. 6A.

Figure 6A:
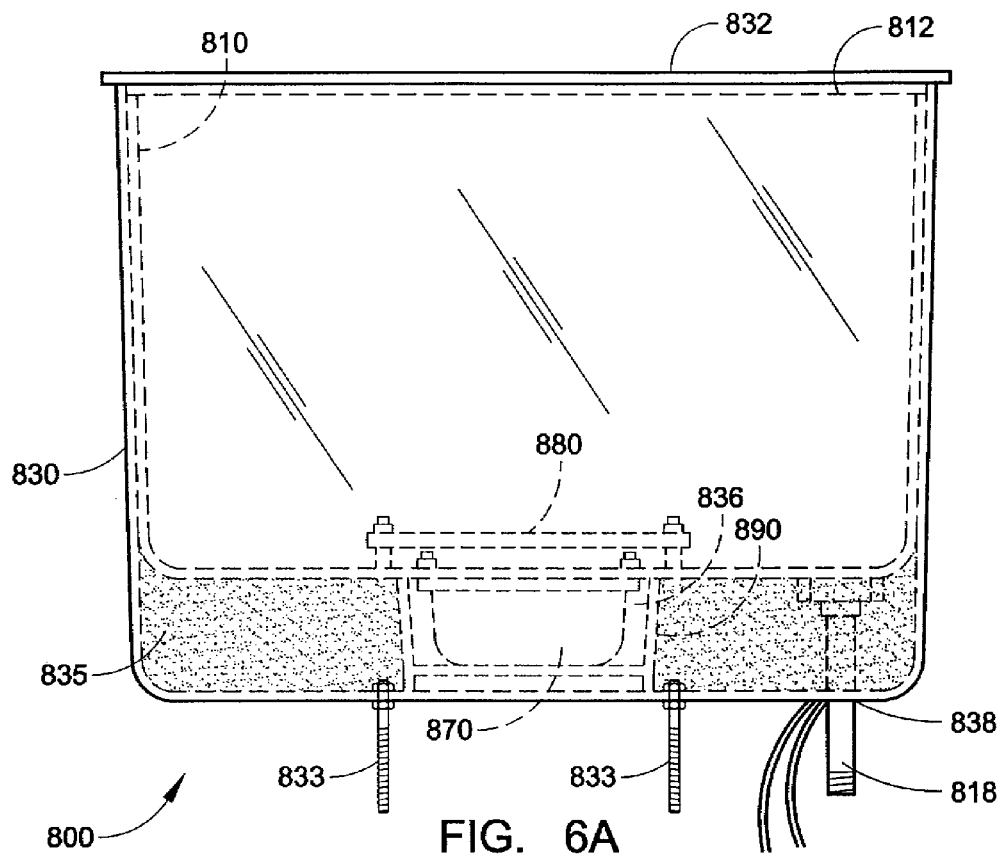
FIG. 6A is a front transparency view of the treatment vessel depicted in FIG. 5.
Figure 6B:
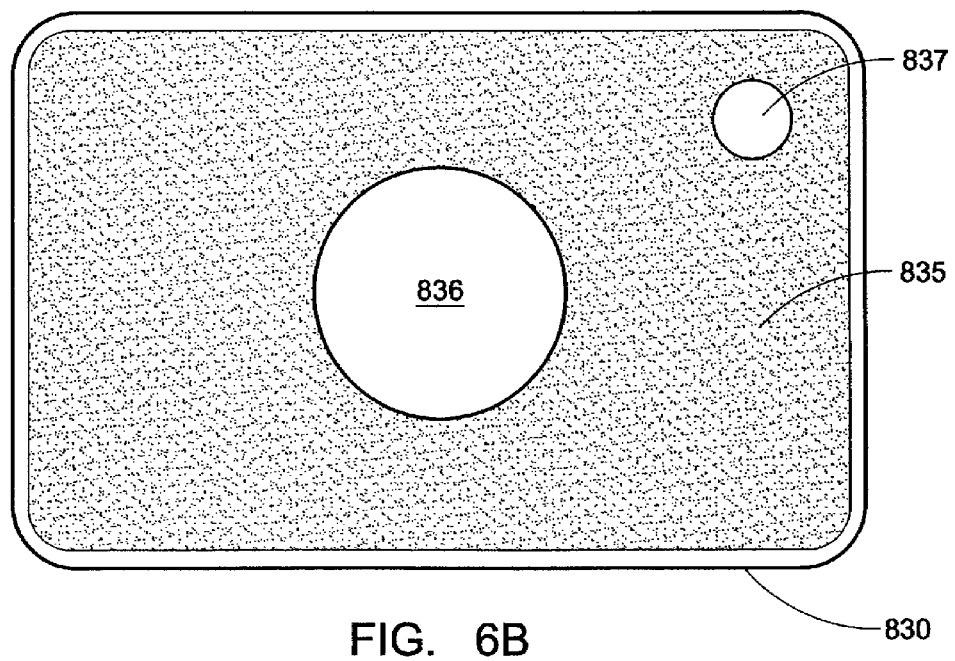
FIG. 6B is a top view of the wound treatment tank depicted in FIG. 5.

The tank 830 is made of a molded plastic or metal that is rigid and durable. As shown in FIGS. 6A and 6B, the tank 830 has a foam platform 835 forming an inner bottom surface of the tank 830. The foam platform 835 has a circular pipe hole 836 cut into it that receives the audio transducer or speaker 870. The foam platform 835 has a second pipe hole 837 cut into it that is matched up with a hole 838 cut in the bottom of the tank 830 to form an outlet port for the water pipe 818 projecting vertically downward from the bottom surface of the chamber 810. Bolts 833 projecting vertically downward from the bottom of the tank 830 are used to guide and connect the tank 830 to the carriage 15.

Figure 7A:
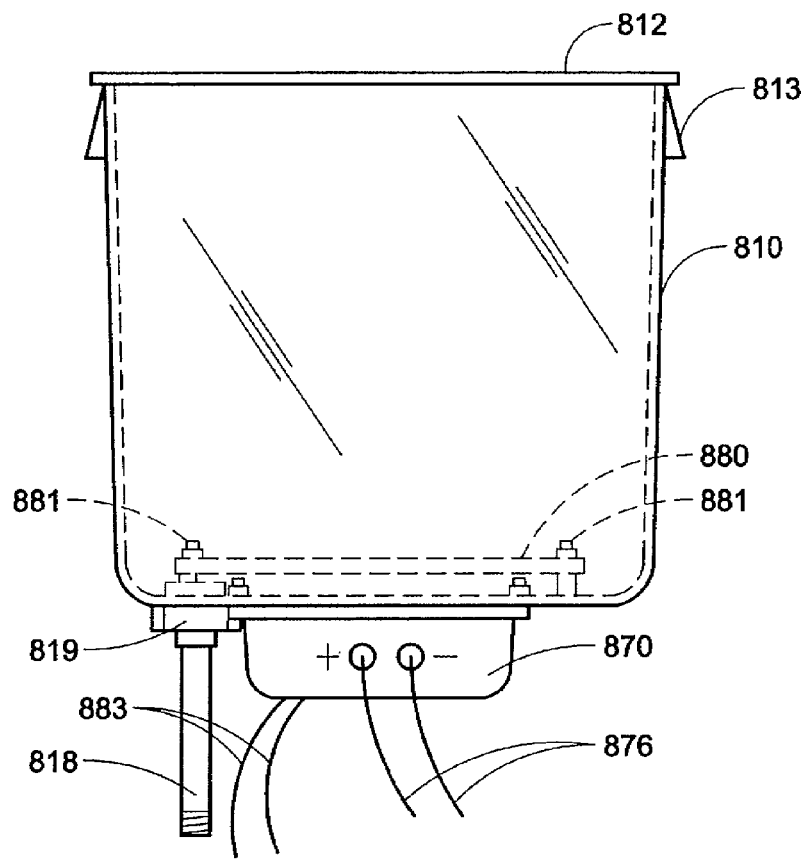
FIG. 7A is a front transparency view of a wound treatment chamber.
Figure 7B:
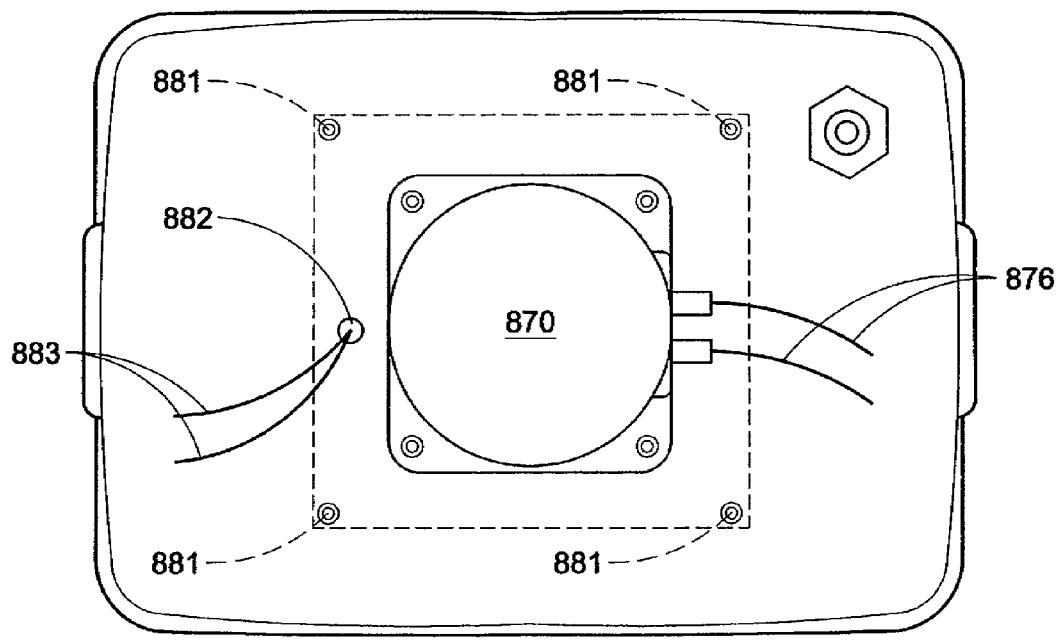
FIG. 7B is a bottom view of the wound treatment chamber depicted in FIG. 7B.

Turning to FIGS. 7A and 7B, chamber 810 is shown in more detail. The chamber 810 includes a sealing member 813 that surrounds the chamber just beneath its edge 812. The sealing member 813 forms a substantially fluid-tight seal between the chamber 810 and the tank 830. Inside the chamber 810 is an IR board 880 with an array of IR LEDs. The board 880 has bolts 881 on its corners that are used to bolt the board 880 to the bottom of the chamber 810. PCB wiring 881 is coupled to the IR board 880 and exits from the chamber 810 through hole 882 drilled into the bottom of the chamber 810. The hole 882 can be drilled at a location beneath the IR board 880 and can be about ¼ inch. Silicone, hot glue, and/or other sealing materials can be used to form a fluid tight seal between the wiring 881 and the hole 882 to seal the chamber 810, hardware, and wires from leaks. The wiring 881 is lead through the pipe hole 837 in the tank 830 and connects with a connection to the control box.

The IR board 880 includes IR LEDs arranged in a pattern on a square or rectangular board. The IR LEDs can emit energy at infrared frequencies of between about 700 nm and 50,000 nm. The IR board 880 can be controlled by the control panel to adjust the frequency. In one embodiment, the IR LEDs deliver about 2000 mW of infrared light at about 810 nm. In one embodiment, the IR board 880 can also generate about 1.2 W of Red light at about 660 nm for a combined total light output of 1911 mW. For example, the IR board 880 can be a Thor DDII IR Lamp System.

Turning to FIG. 7A, a hole is drilled through the bottom of the chamber 810, and the water pipe 818 is inserted through the hole, projecting vertically downward through the hole and out the bottom of the chamber 810. A tub seal pipe coupling 819 is used to form a fluid tight seal between the pipe 818 and the hole through which it is inserted through the chamber 810. The water pipe 818 is open at both ends to allow water to flow in and out of the chamber 810 when the chamber 810 is connected to the reservoir 600 through a water hose.

As shown in FIGS. 7A and 7B, coupled to the outside of the chamber at the bottom of the chamber 810 is an audio transducer or speaker 870. The speaker 870 is bolted to the bottom of the chamber 810. Transducer wires 876 are connected to the speaker 870 and, like the IR wiring, are threaded through the pipe hole 837 in the tank 830 to form a connection with the control box. As shown in FIGS. 5 and 6A, a rigid plastic or metal collar 890 with a hole 892 is placed around the speaker 870 to protect the speaker 870. The speaker 870 emits energy at a low frequency sound wave of between about 1 Hz and about 1000 Hz. In one embodiment, the speaker emits energy at about 60 Hz. This causes a therapeutic vibration on the chamber 830 and a massaging effect on the patient's limb.

In one embodiment the foam platform 835 is a premolded piece that is inserted into the bottom of the tank 810, and the chamber 810 is placed on top of the foam 835. In another embodiment, a hardening foam gel is poured into the bottom of the tank 810 to a predetermined depth, and the chamber 810 with speaker 870 and collar 890 are quickly placed into the tank 810. The foam gel hardens around the pipe 838 and wires 881 and 876, the collar 890, and the bottom of the chamber 810. The tank 830 is ultimately bolted to the rigid plastic carriage 15.

Figure 8A:
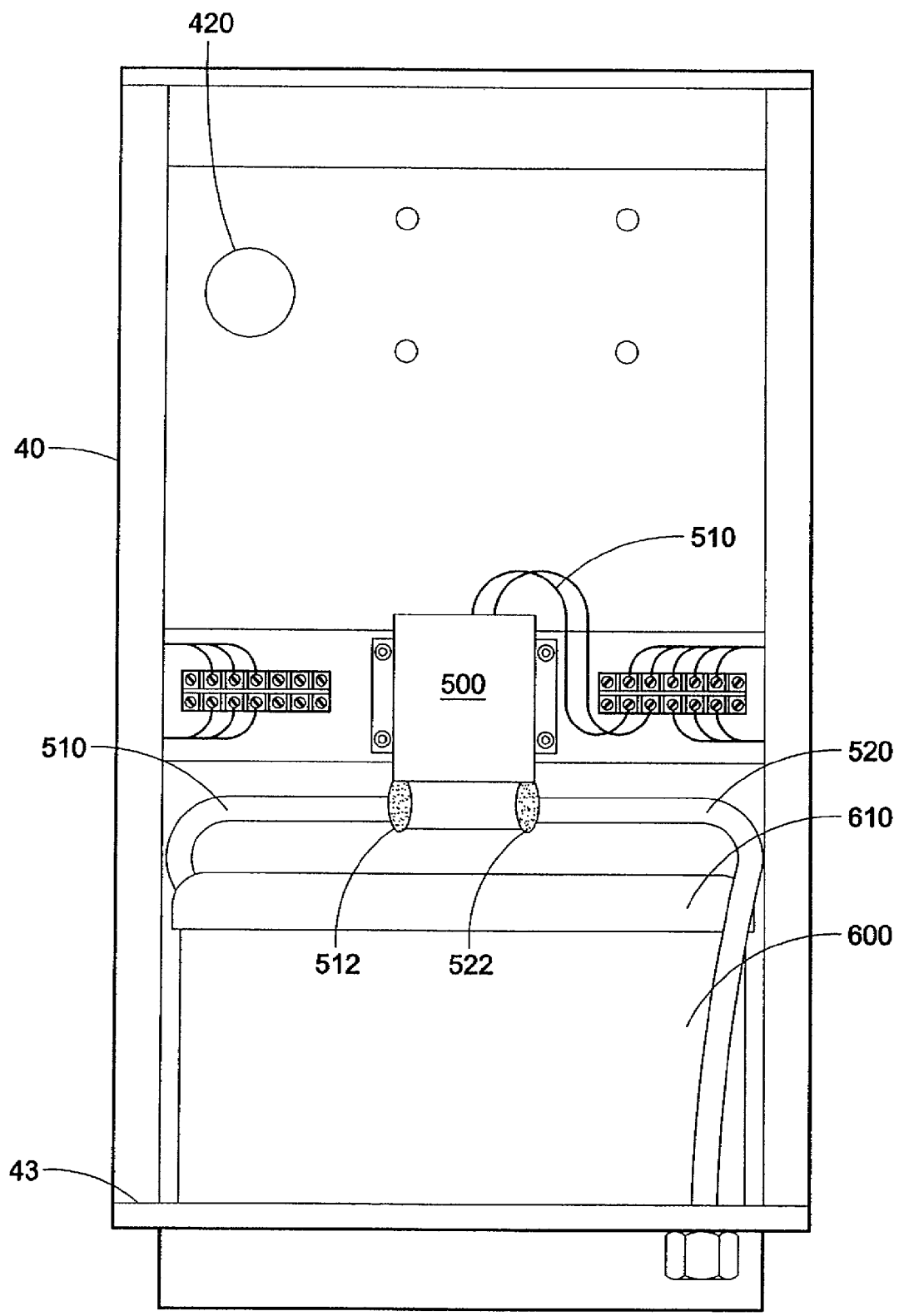
FIG. 8A is a rear view of a wound treatment system with a rear panel removed.
Figure 8B:
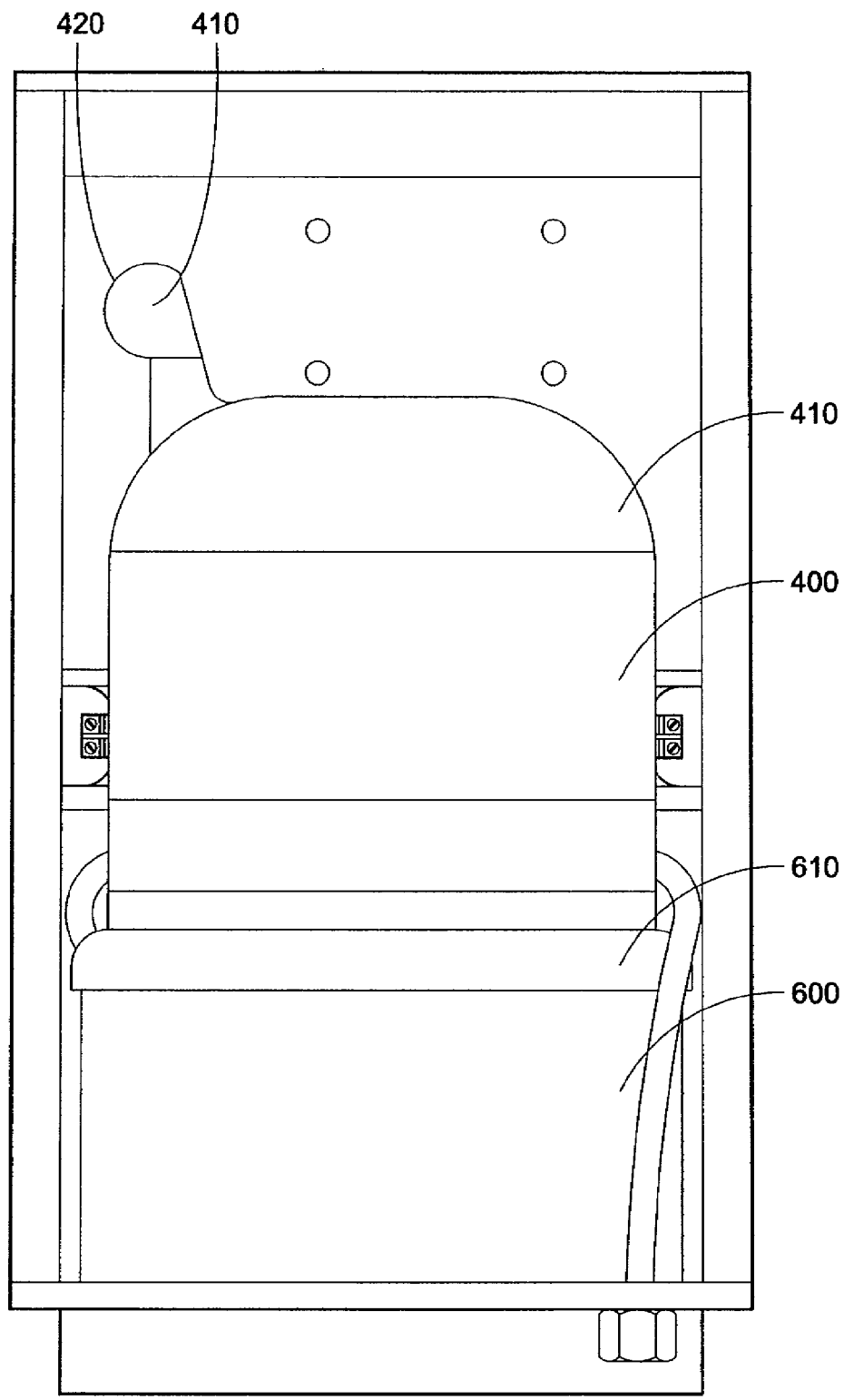
FIG. 8B is another rear view of the wound treatment system depicted in FIG. 8B further depicting a humidifier.

Now turning to FIGS. 8A and 8B, the components of the wound treatment system 10 that are housed in the cart 40 are shown. Both FIGS. 8A and 8B are front views of the cart 40 looking at the cart 40 from the direction of viewing the control panel 30. FIG. 8A shows the components with the humidifier 400 removed so that the water pump 500 is visible. FIG. 8B shows the components with the humidifier 400 in its normal position blocking a view of the pump 500, which sits behind the humidifier 400.

As shown in FIG. 8A, a warm water reservoir 600 rests on a shelf 43 at the bottom of the cart 40. A first hose 510 is connected to the water pump 500 through fitting 512. The other end of the hose 510 is secured to a hose fitting 630 (shown in FIG. 9B) laterally projecting from the reservoir 600 so that the hose is in fluid communication with the inside of the reservoir 600. A second hose 520 is connected to the water pump 500 through fitting 522. The other end of hose 520 is connected to the water pipe 818 projecting vertically from the bottom of the vessel 800 so that the hose 520 is in fluid communication with the inside of the chamber 810. Cables 510 electrically couple the water pump to the control box. The reservoir 600 has a rigid lid 610 that can be removed to expose the inside of the reservoir and fill it with water.

Figure 9A:
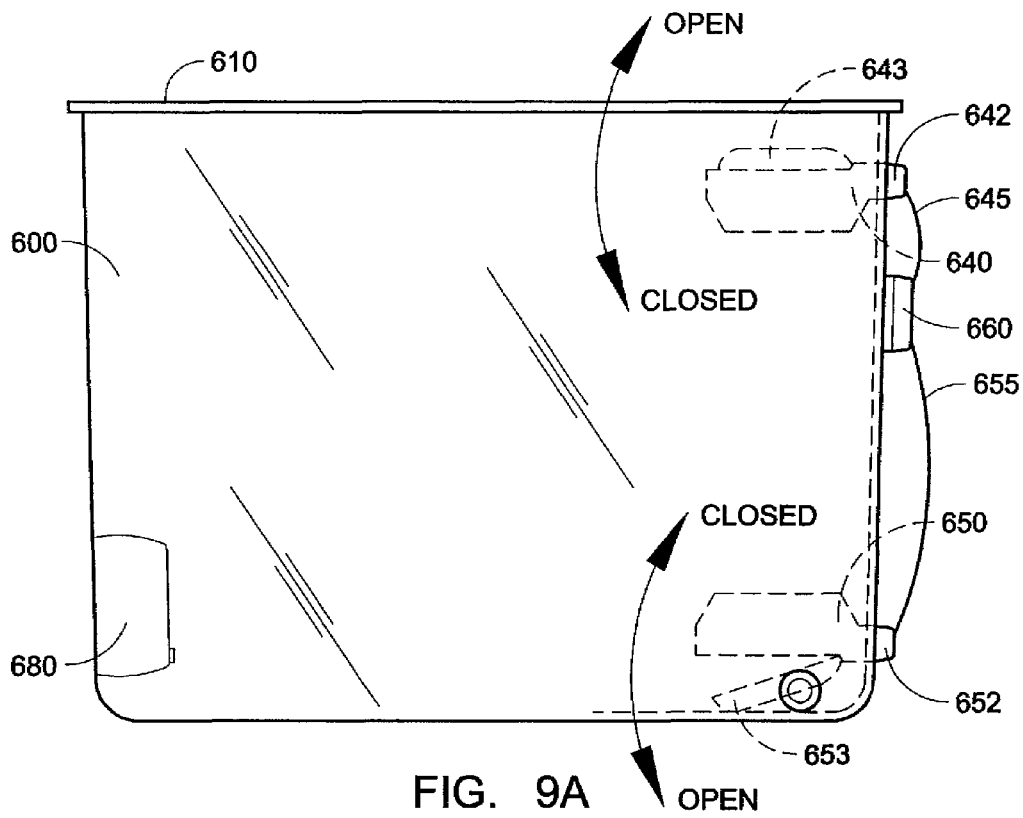
FIG. 9A is a front transparency view of a water reservoir used in a wound treatment system.
Figure 9B:
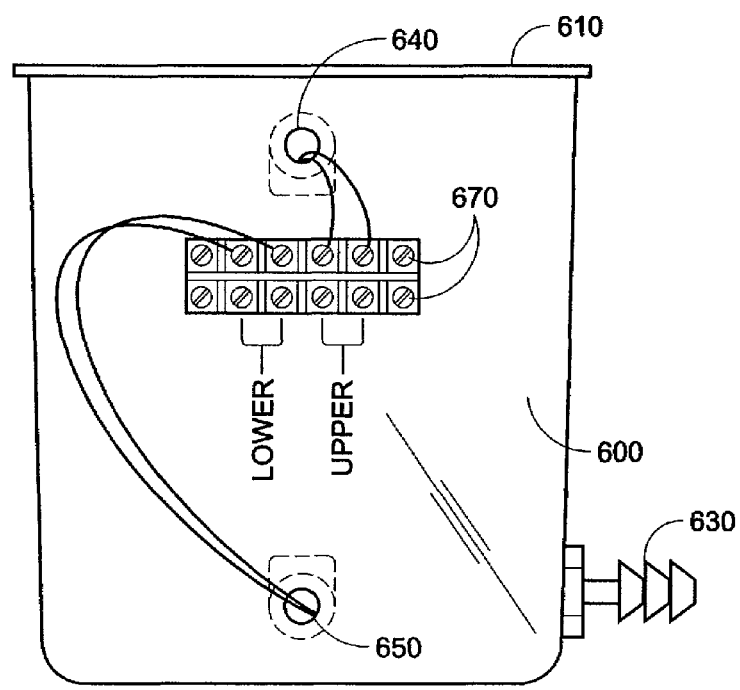
FIG. 9B is a side transparency view of the water reservoir depicted in FIG. 9A.

Turning to FIGS. 9A and 9B, the reservoir 600 is shown in more detail. The reservoir 600 includes two float twitches 640 and 650. An upper float switch 640 is used to determine when the reservoir 600 is full and a lower float switch 650 is used to determine when the reservoir 600 is empty. Switch 640 has a lead 642 that is electrically connected to terminal block 660 with wire 645. Switch 650 has a lead 652 that is electrically connected to terminal block 660 with wire 655. Terminal block 660 is electrically connected to the pump with wires 670. The spacing between the switches 640 and 650 determines the amount of water that will be pumped into the chamber 830 when the system 10 is activated and the pump function is operating. The switches 640 and 650 are arranged so that the optimal amount of water is pumped into the chamber 830. If too much water is pumped into the chamber, the lid 61 can dislodge causing the chamber 830 to leak. If there isn't enough water, the patient's limb will not be warmed enough. In one embodiment, about five gallons of water is pumped from the reservoir 600 to the chamber 830. When the pump function is activated, the pump begins to pump water 500 out of the reservoir 600 through fitting 660. When the water level reaches the lower switch 650 and the floating arm 653 of the switch 650 begins to dip fall, an electrical signal is transmitted to the pump 500 through wires 670, and the pump 500 automatically shuts off. When the drain function is activated, the pump 500 begins to pump in reverse, draining the water from the chamber 830 and back into the reservoir 600. When the water in the reservoir reaches the upper switch 650 and the floating arm 643 of the switch 640 begins to rise, an electrical signal is transmitted to the pump 500 through wires 670, and the pump automatically turns off.

In one embodiment, the water is kept at an optimal temperature with a portable heating unit 680 that is adjustable between a range of about 70° F. and about 90° F. In another embodiment, a more sophisticated heating unit is used (not shown) that is electrically coupled to the control box and can be controlled with a thermostat in the control panel 30.

Turning back to FIG. 8B, the humidifier unit 400 sits atop the lid 610 of the reservoir 600. The humidifier has a removable lid 410 that can be removed to fill the reservoir of the humidifier 400 with water and an antibacterial agent, such as ionic silver, hydrogen peroxide, bacitracin, betadine, or isopropyl alcohol. In one embodiment, adiabatically humidified 1% hydrogen peroxide/silver solution is used, but other FDA approved topical antibacterial, antibiotic, antiseptics and antimicrobial solutions and agents, such as those described above, may also be used.

The humidifier 400 has a misting unit that constantly produces mist as long as the humidifier function on the control panel 30 is activated. The misting unit can be an adiabatic temperature controlled humidifier or ultrasonic nebulizer. The humidifier 400 can generate room temperature mist or heated mist. It can include a built-in heater (not shown) with an on/off switch and an indicator light that shows that the heater is on and at operating temperature. Warm mist temperature in the bag 100 can reach between about 77° F. and about 82° F. as measured with a temperature gauge in the lid assembly. The humidity in the bag 100 can reach about 89% to about 91% as measured by a humidity gauge. The humidifier has a transducer that generates ultrasonic energy at about 40 kHz to create an adiabatic/humid mist that creates a cloud. Ultrasonic energy from the misting unit is not transmitted to the limb, which is about two feet away from the misting unit. When the valve control unit 50 is opened, the mist travels from the humidifier 400 into the exit tube 410 and out through the exit port 420 where it enters the valve control unit 50. From there the mist travels through the tube 70 and into the treatment zone formed by the bag 100 surrounding the patient's limb.

Other embodiments are within the scope of the following claims.

What is claimed is:

1. A method for treating diabetic foot ulcers, comprising:
   (a) introducing a human foot having a foot ulcer into a treatment chamber;
   (b) surrounding the foot in the treatment chamber with a mist containing water and an antibiotic; and
   (c) surrounding the foot in the treatment chamber with an $O_2$-enriched gas without increasing the pressure around the foot to 22 mm Hg.

2. The method of claim 1, wherein steps (b) and (c) are performed sequentially multiple times in a single treatment.

3. The method of claim 1, wherein the antibiotic is a topical antibiotic.

4. The method of claim 1, wherein said antibiotic is selected from betadine, isopropyl alcohol, bacitracin, and hydrogen peroxide, and combinations thereof.

5. The method of claim 1, wherein said antibiotic is ionic silver.

6. The method of claim 1, wherein the treatment chamber is a disposable plastic bag, further comprising sealing the bag about the leg in such a manner that the mist and the oxygen can surround the foot.

7. The method of claim 1, wherein the $O_2$ displaces the mist.

8. The method of claim 1, wherein the $O_2$ is substantially pure $O_2$.

9. The method of claim 1, wherein said method further comprises repeating the treatment periodically until the foot ulcer is healed.

10. The method of claim 1, wherein said treatment chamber comprises a foam cuff adapted to seal around a human leg.

11. The method of claim 1, wherein step (b) is performed for about 2 to about 30 minutes.

12. The method of claim 11, wherein step (b) is performed for approximately 15 minutes.

13. The method of claim 1, wherein step (c) is performed for about one minute to about 15 minutes.

14. The method Of claim 13, wherein step (c) is performed for approximately 5 minutes.

15. The method of claim 2, wherein steps (b) and (c) are performed 4 times, the single treatment lasting approximately 80 minutes.

16. The method of claim 1, wherein said mist is an adiabatic mist.

17. The method of claim 1, wherein steps (b) and (c) are performed simultaneously.

18. The method of claim 1, wherein steps (b) and (c) are performed sequentially.

19. The method of claim 1, further comprising massaging the foot with low frequency sound waves.

20. The method of claim 1, further comprising heating the foot with pulsed light.

* * * * *